(12) United States Patent
Plant

(10) Patent No.: US 7,446,871 B2
(45) Date of Patent: Nov. 4, 2008

(54) METHOD AND APPARATUS FOR REAL-TIME POLARIZATION DIFFERENCE IMAGING (PDI) VIDEO

(76) Inventor: James Plant, 4504 Bissenden Place, Victoria, British Columbia (CA) V8N 3K4

( * ) Notice: Subject to any disclaimer, the term of this patent is extended or adjusted under 35 U.S.C. 154(b) by 180 days.

(21) Appl. No.: 11/476,335

(22) Filed: Jun. 28, 2006

(65) Prior Publication Data
US 2007/0034803 A1 Feb. 15, 2007

Related U.S. Application Data

(60) Provisional application No. 60/695,551, filed on Jun. 30, 2005.

(51) Int. Cl.
G01J 4/00 (2006.01)
(52) U.S. Cl. .................... 356/364
(58) Field of Classification Search .............. None
See application file for complete search history.

(56) References Cited
U.S. PATENT DOCUMENTS
5,975,702 A 11/1999 Pugh, Jr. et al.

2002/0054290 A1* 5/2002 Vurens et al. ............ 356/369
2006/0192960 A1* 8/2006 Rencs et al. ............. 356/364

FOREIGN PATENT DOCUMENTS

GB 2 153 071 A 8/1985
JP 9-145329 6/1997

* cited by examiner

Primary Examiner—Michael P Stafira
(74) Attorney, Agent, or Firm—Davis Bujold & Daniels, P.L.L.C.

(57) ABSTRACT

A method and apparatus for real-time polarization difference imaging (PDI) video including an imaging lens focusing the light on to a collimating lens, whereby the stimulus beams becomes parallel before striking a polarizing beam-splitter. Segregated orthogonally polarized components of the stimulus are then focused on imaging sensors, and one sensor's output signal is subtracted from the other, thereby creating a real-time polarization difference video image. The efficiency of such a system is greatly enhanced by illuminating the target with a polarized light source (with a polarization orientation matching one of those used in the PDI process), and PDI-enhanced targets can be constructed with surface features and textures optimised to result in a maximum return signal strength and spatial contrast.

11 Claims, 9 Drawing Sheets

METHOD AND APPARATUS FOR REAL-TIME POLARIZATION DIFFERENCE IMAGING (PDI) VIDEO

This application claims priority from U.S. Provisional Application Ser. No. 60/695,551 filed Jun. 30, 2005.

FIELD OF THE INVENTION

The present invention relates to a method and an apparatus for real-time polarization difference imaging (PDI) video.

BACKGROUND OF THE INVENTION

Polarization imaging systems have typically been complex, expensive, and unsuitable for applications in harsh environments. The technique of Polarization Difference Imaging (PDI) requires that two or more images must be taken (sensing different or orthogonal planes of polarization within a stimulus), and the spatial difference in intensity of the recorded images be determined by the subtraction of one image from the other.

Typically PDI systems have either utilized mechanically rotated optical polarizers, or more recently, electrically tunable liquid crystal polarizers. In both cases, the resultant "difference image" includes the amount of polarized light that is reflected directly off the surface of the object, and (because of common mode rejection of randomly polarized light) the veiling effects of scattering caused by intervening medium such as smoke, fog, or suspended particulates in fluids is subtracted.

It has been demonstrated that even if less than 1 percent of the returning light from the target is polarized, a PDI image can be made which can reveal even subtle surface details and textures. PDI therefore can greatly enhance target detection and by substantially enhancing contrast and reducing noise in the presence of intervening scattering medium or mechanisms. For example, in underwater imaging, PDI has been shown to extend the distance at which objects can be imaged by a factor of three.

Common to all existing PDI systems is the requirement to take two distinct polarization images separated in time. As a result, creating a "real-time" PDI video system has been problematic.

SUMMARY OF THE INVENTION

According to one aspect there is provided an apparatus for real-time polarization difference imaging (PDI) video. The system includes means for collimating stimulus light into parallel beams of light. At least one polarizing beam splitter is provided which is adapted to receive collimated beams of light and create segregated orthogonally polarized components of the beams of light. Sensors are provided for sensing the segregated orthogonally polarized components of the beams of light. Means are provided for subtracting one of the sensor's output signal from another of the sensor's output signal and creating a real-time polarization difference video signal.

According to another aspect of the present invention there is provided a method of real-time polarization difference imaging (PDI. A first step involves collimating beams of light so that the stimulus beams of light become parallel. A second step involves passing the parallel beams of light through at least one polarizing beam-splitter to create segregated orthogonally polarized components of the beams of light. A third step involves focusing the segregated orthogonally polarized components of the beams of light upon sensors. A fourth step involves subtracting one of the sensor's output signal from another of the sensor's output signal to create a real-time polarization difference video signal.

BRIEF DESCRIPTION OF THE DRAWINGS

These and other features of the invention will become more apparent from the following description in which reference is made to the appended drawings, the drawings are for the purpose of illustration only and are not intended to in any way limit the scope of the invention to the particular embodiment or embodiments shown, wherein.

DETAILED DESCRIPTION OF THE PREFERRED EMBODIMENT

The preferred embodiment, a "Real-Time" Polarization Difference Imaging (PDI) Video System will now be described with reference to FIGS. 1 through 9.

Figure 1:
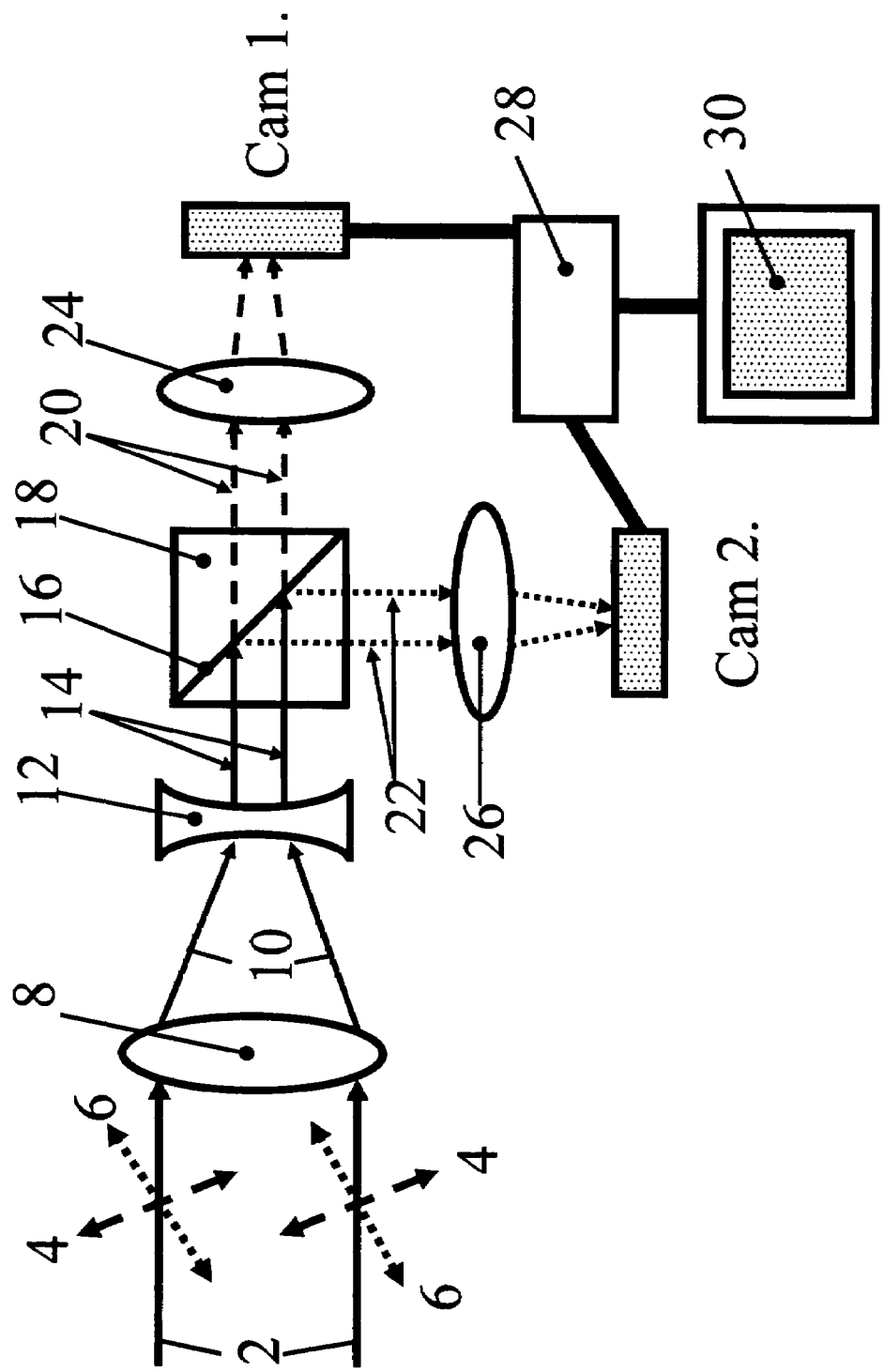
FIG. 1 is a schematic illustration of the spatial and functional relationship between the major components of the real-time PDI video system.
Figure 2:
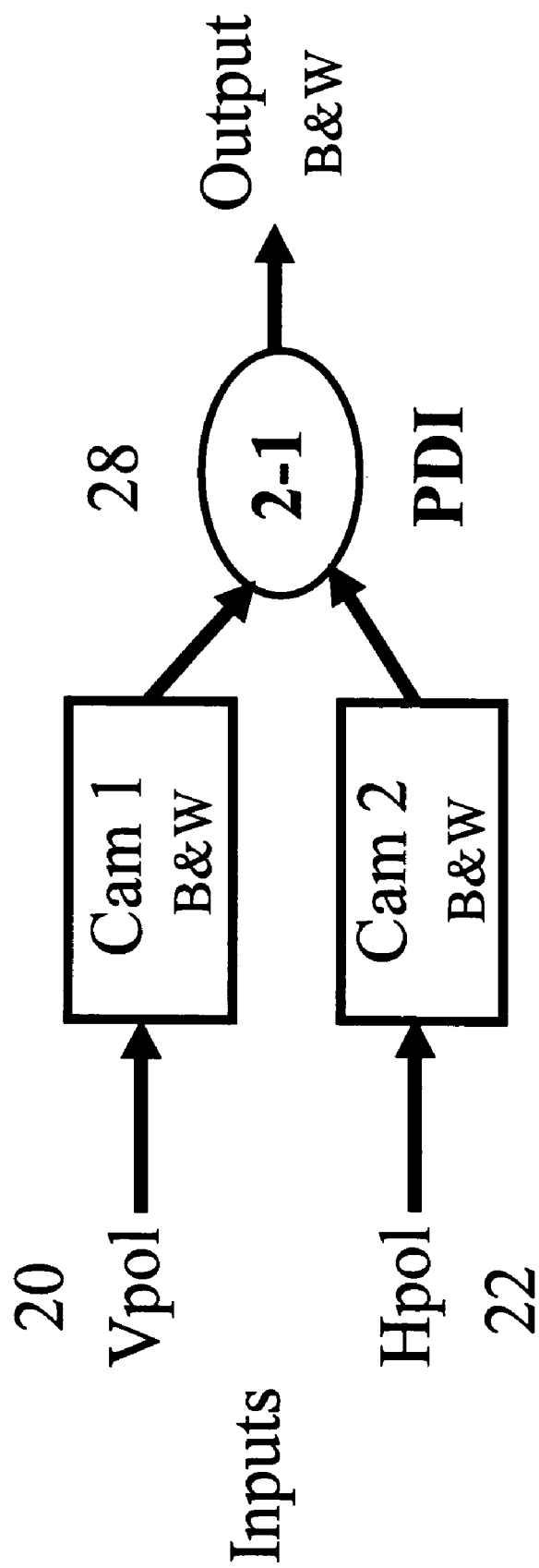
FIG. 2 is a flow chart illustrating the process and mode of operation where PDI video can be used to highlight subtle spatial variations in surface textures or geometry of the imaged target.
Figure 3:
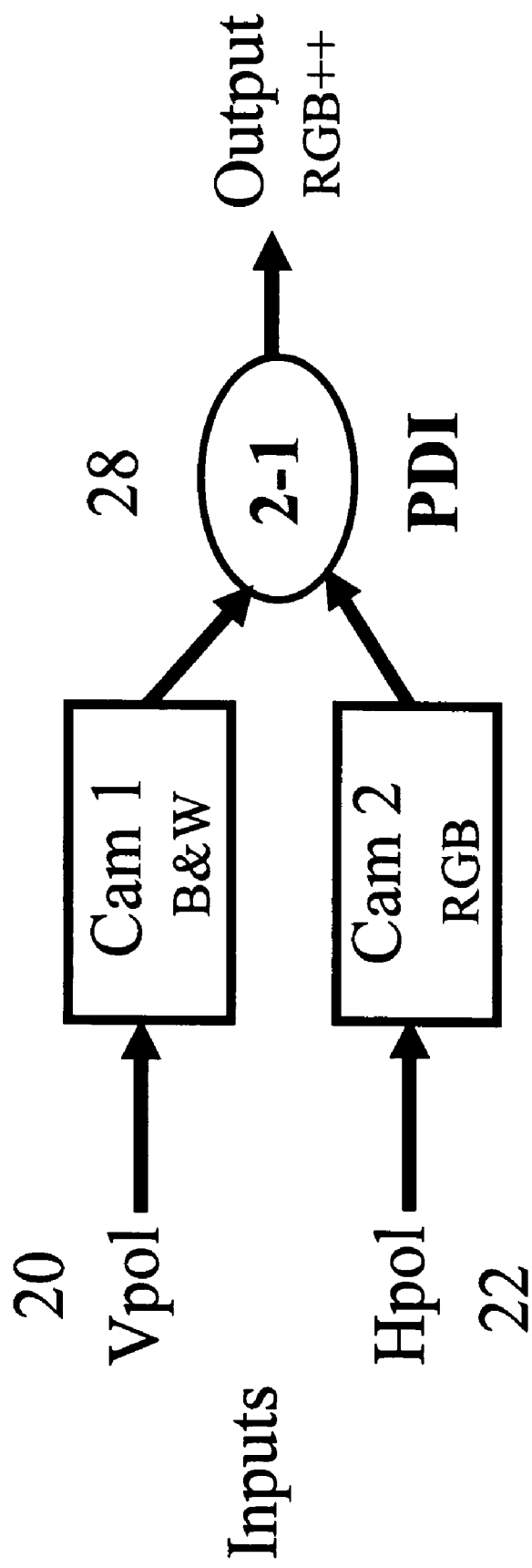
FIG. 3 is a flow chart illustrating the process and mode of operation where PDI video can be used to highlight subtle spatial variations in corrosion of metal surfaces.
Figure 4:
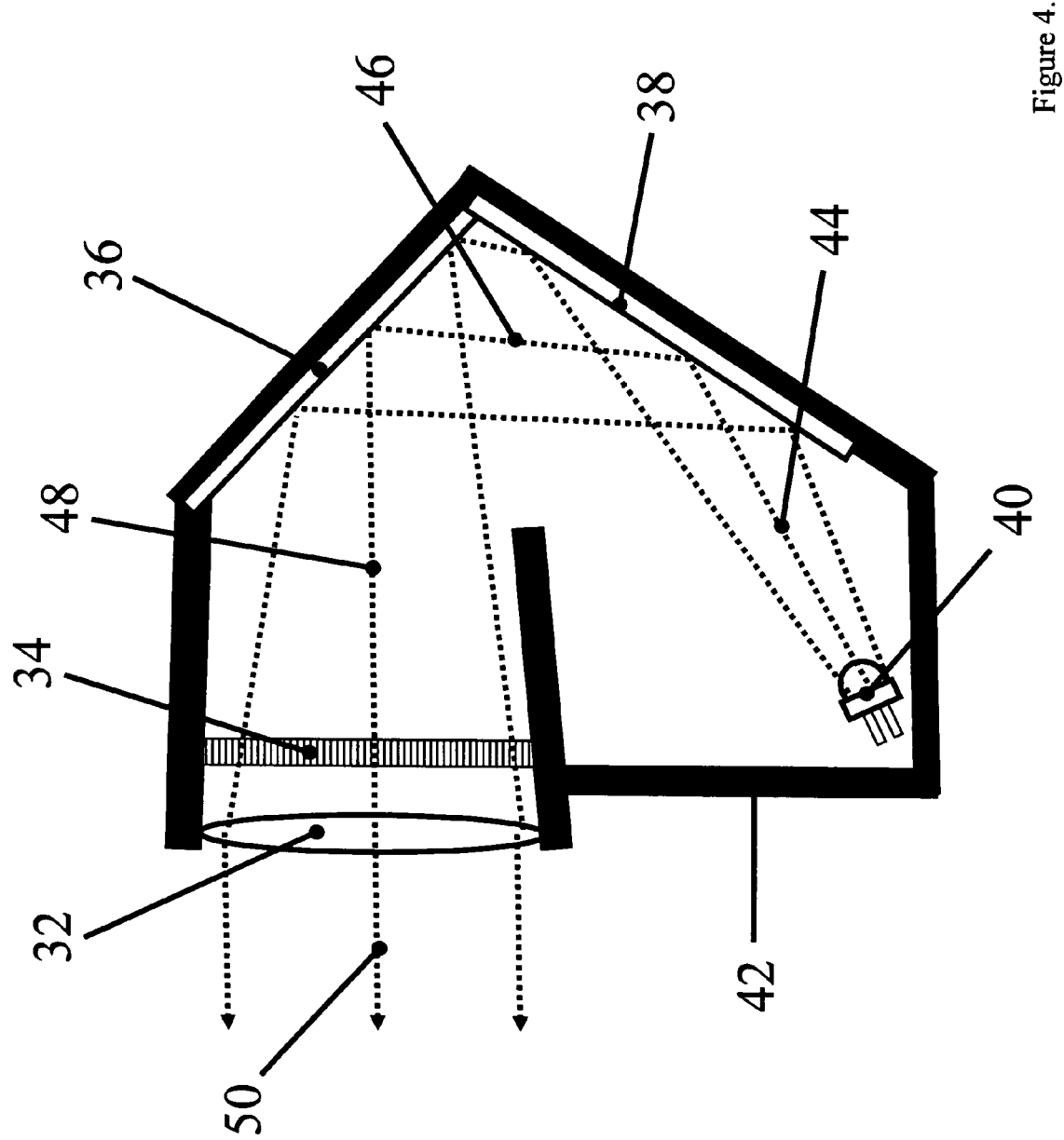
FIG. 4 is a schematic illustration of the spatial and functional relationship between the major components of the polarized light source used to enhance PDI imaging.

The present invention represents a real-time polarization difference imaging (PDI) video system which functions by selectively segregating at least two orthogonal planes of polarized light from an input image, focuses these polarization specific images on to separate video cameras, and subtracts one of the polarization specific images from the other thereby resulting in a real-time PDI video output. To enhance the contrast between the simultaneous orthogonal polarization images, a polarized light illumination system is presented which can be used to illuminate the target object to be imaged. By varying the radial orientation of the polarization illumination and sensors to match the planar geometry of target surface or features, the intensity of the returned signal can be maximized, thereby enhancing target isolation in the presence of scattering medium or mechanisms, or intervening (obscuring) objects with different polarization reflectance properties (such as foliage). Utilizing the underlying principle of this real-time PDI video system, PDI enhanced targets and signs can be developed which greatly increase the PDI return signal under ambient or polarized illumination. Common to all existing PDI systems is the requirement to take two distinct polarization images separated in time. As a result, creating a "real-time" PDI video system has been problematic. The present PDI system, being structurally based, and allowing simultaneous acquisition of orthogonal planes of polarization from within a common input, is uniquely capable of generating "real-time" PDI video signals without the requirement of additional complex and expensive mechanical or electrical systems. The system includes an imaging (FIG. 1, item 8.) and collimating lens (FIG. 1, item 12) system which projects an image of the target object through a polarizing beam splitter cube (FIG. 1, item 18) thereby separating the horizontally and vertically-polarized components of the incident beam (FIG. 1, items 6 and 4 respectively) into two orthogonal beams which exit the polarization cube at 90 degrees to each other (FIG. 1, items 22 and 20). These separate beams then pass through lenses (FIG. 1, items 26 and 24) focus them onto separate (digital or analogue) video cameras (FIG. 1, items Cam 1 and Cam 2). The camera's respective polarization specific video outputs are digitally aligned, and are processed using standard video subtraction techniques to create a "real-time" PDI video image.

We have determined that the spatial resolution and general image quality of PDI images can be significantly enhanced by illuminating the target object with a polarized light source. Unlike applications which utilized polarized light illumination to detect light scattered off a surface, we utilize polarized illumination to specifically isolate and enhance the contrast between light directly reflected off the surface of the target object, and the light scattered by intervening mechanisms or mediums. By adjusting the axial orientation of the polarization illumination source (and its specific wavelength), a detailed spatial mapping of different characteristics of surface textures or deviations in the surface geometry can be undertaken.

Brewster's angle is the angle of incidence of electromagnetic radiation at which 100 percent of the radiation with a polarization parallel to the material's face is reflected. With transmissive materials, Brewster's angle is equal to the Arc Tangent of the material's refractive index for a given wavelength. Utilizing this proven optical principle, polarizing beam-splitters (such as Glan Taylor Prisms) have been constructed.

FIG. 1.

In-coming illumination (2) contains various orientations of polarized light, of which only the horizontal (6) and vertical (4) components are shown for clarity of presentation. The stimulus passes through an imaging lens (8), and the converging beams (10) strike a collimating lens (12), resulting in parallel beams (14) entering a polarizing beam splitter (18). This collimation of the in-coming stimulus is critical so that all input strikes the internal reflective surface of the prism (16) at Brewster's Angle. The result is that the horizontally polarized components of the input stimulus are reflected down ninety degrees (22), and the vertically polarized component of the stimulus carries straight through the prism (20). The segregated horizontally polarized component then passes through a focusing lens (26) and the input image is projected onto a video camera chip (Cam.2). Likewise, the vertically polarized component (20) passes through a focusing lens (24), and the input image is projected on a second video camera chip (Cam.1). The output of the cameras are then sent to a video processing circuit (28) that subtracts one input from the other (thus creating a polarization difference image), and the resultant output is displayed on a standard video monitor or computer (30). Although "vertical" and "horizontal" components have been referred to, it is important to understand that the components need only be orthogonal to each other, they do not have to be vertical and horizontal within the strict means of those terms.

In contrast to existing polarization filters, (which can sample only one plane of polarization at a time), the polarizing beam splitter's physical structure allows for simultaneous real-time sensing of two polarization planes. Polarization Difference Imaging (PDI) can then be applied to; (a) enhance contrast and reduce noise in the presence of intervening scattering medium, (b) detect the presence and estimate the degree of scattering in an intervening medium, and (c) greatly enhance the range and reliability of free space optics data transmission systems.

FIG. 2.

Using PDI imaging to detect the presence (and identify) an object obscured by scattering medium (if colour information is not critical), or for detailed observation of textural and structural surface features, a PDI video system operating in Black and White (B&W) mode has the greatest utility. In this, (and FIG. 3.), the orientation of the polarized illumination is horizontal. Had the illumination been vertically polarized, the greatest return signal would be achieved by subtracting Cam 2's input from Cam 1.

FIG. 3.

Illustrates a mode of operation of the PDI video system that maximizes its utility for the detection of rust, pitting, or other signs of metal corrosion in the presence (or absence) of scattering medium. In this mode of operation, the video stream from the camera conveying the strongest return input (in this case Cam 2.) is operated in full colour mode. As a result, when the black and white video stream of Cam 1. is subtracted, the magnitude of its grey values are subtracted from Cam 2's colour space. This creates a PDI image with enhanced colour intensity and saturation which is uniquely suited to the detection, characterization and spatial mapping of corrosion on metal. Even subtle distinctions between areas of rust and pitting, and surface discolouration can be seen, while the PDI process allows for this imaging to be done through scattering medium such as murky water.

FIG. 4.

Polarized light sources (other than lasers) most often make use of the fact that light typically contains all orientations of polarization. To create the desired polarization, a polarizing filter is placed in the light path, which allows only the desired orientation of polarized light to pass. Such a subtractive method often significantly decreases stimulus throughput as the selectivity and efficiency of the polarization filter increases. The PDI illumination light source illustrated in FIG. 4. makes use of the fact that light striking a reflective surface at a shallow angle (FIG. 4; items 36 and 38) tends to become polarized. For example, sunlight reflecting off water or a wet road tends to become horizontally polarized, and thus its glare can be effectively decreased by utilizing vertically oriented polarization filters on sunglass lenses. Using this principle, a non-polarized (in this case an IR LED) light source (40) is positioned to shine upon an IR enhanced front surface mirror (38). Since the illumination (44) strikes the mirror at a shallow angle, this has the effect of horizontally polarizing the reflected rays (46). These rays are then reflected off a second mirror (36), again enhancing the horizontal polarization of the reflected light, and these rays (48) are first passed through a horizontal polarization filter (34), then a collimating lens (32). Since the light has been significantly horizontally polarized by internal reflections prior to passing through the polarizing filter (34), the output (50) of this form of polarization illumination system is significantly enhanced. To alter the orientation of polarization to vertical, one simply has to rotate the whole case (42), ninety degrees around the optical axis.

FIG. 5.

Creating targets which have structural or surface qualities that are designed to maximize the strength and spatial resolution of the returned PDI signal can vastly enhance the efficiency and effectiveness of any PDI system. In this figure, an airport taxi sign (52) is illustrated that maximizes contrast by having a background (54) that produces a strong (polarization-dependent) PDI return signal. In contrast, the symbols and lettering on the sign (56) reflect all polarization orientations equally, thus resulting in a low PDI signal due to common mode rejection during the PDI processing.

FIG. 6.

Figure 5:
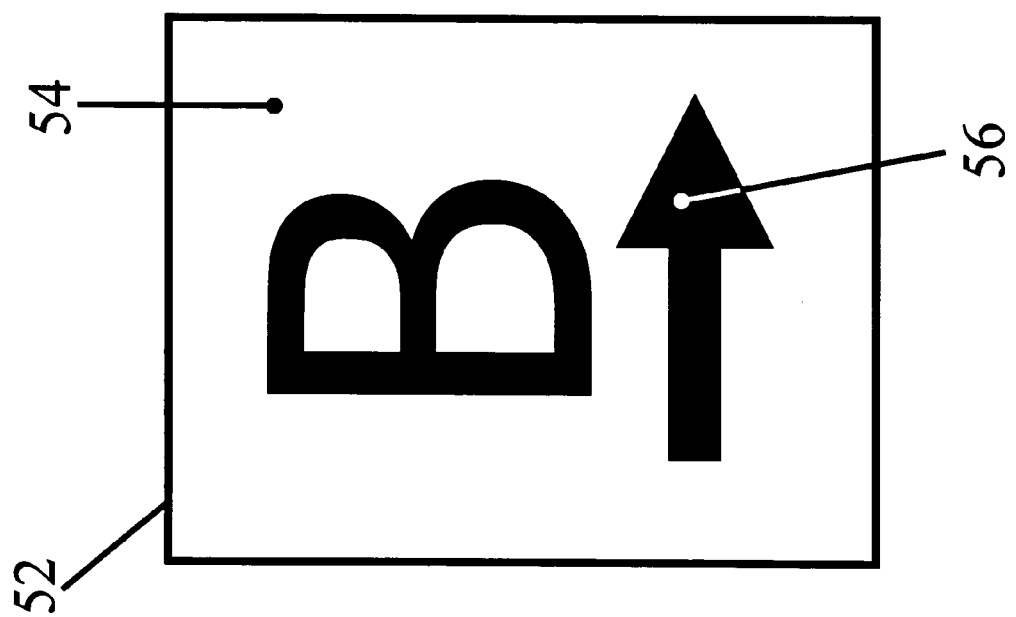
FIG. 5 is a schematic illustration of a PDI-enhanced sign with maximum contrast between the background (strong PDI return signal) and the lettering (weak PDI return signal).

As in FIG. 5, a PDI enhanced sign is illustrated (52) which has structural or surface qualities designed to maximize the PDI return signal's strength and spatial resolution. In this case, the background of the sign (56) is constructed in such a way as to minimize the PDI return signal (through common mode rejection), thereby allowing the greatest contrast of the letters and symbols (54) with strong polarization-dependent reflection.

FIG. 7.

Figure 6:
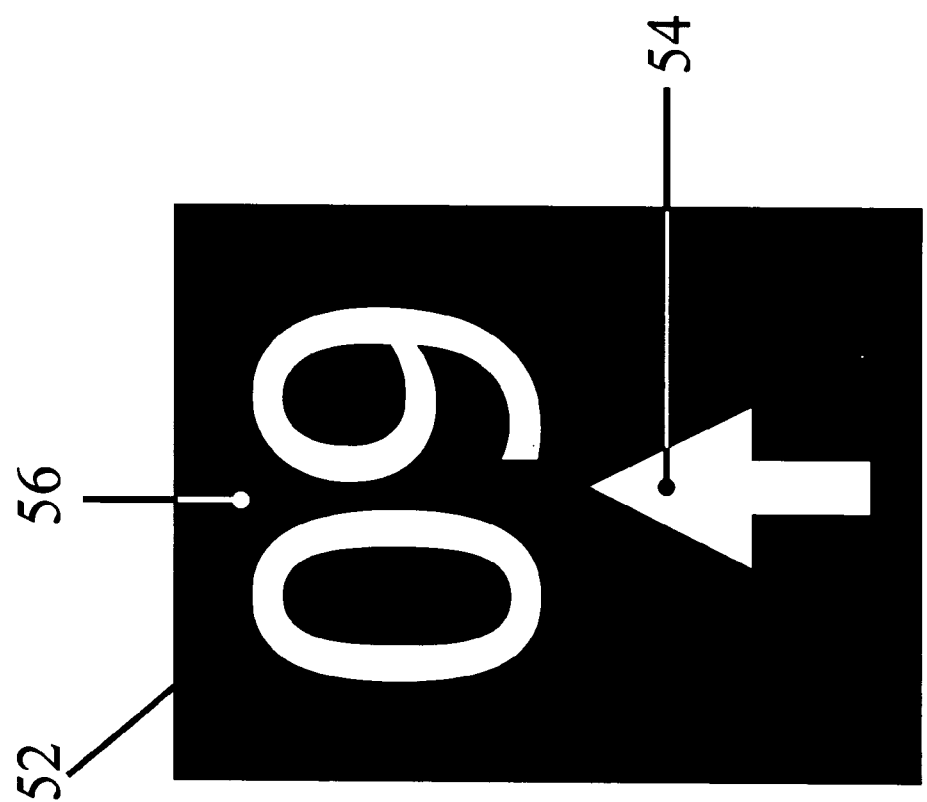
FIG. 6 is a schematic illustration of a PDI-enhanced sign with maximum contrast between the background (weak PDI return signal) and the lettering (strong PDI return signal).
Figure 7:
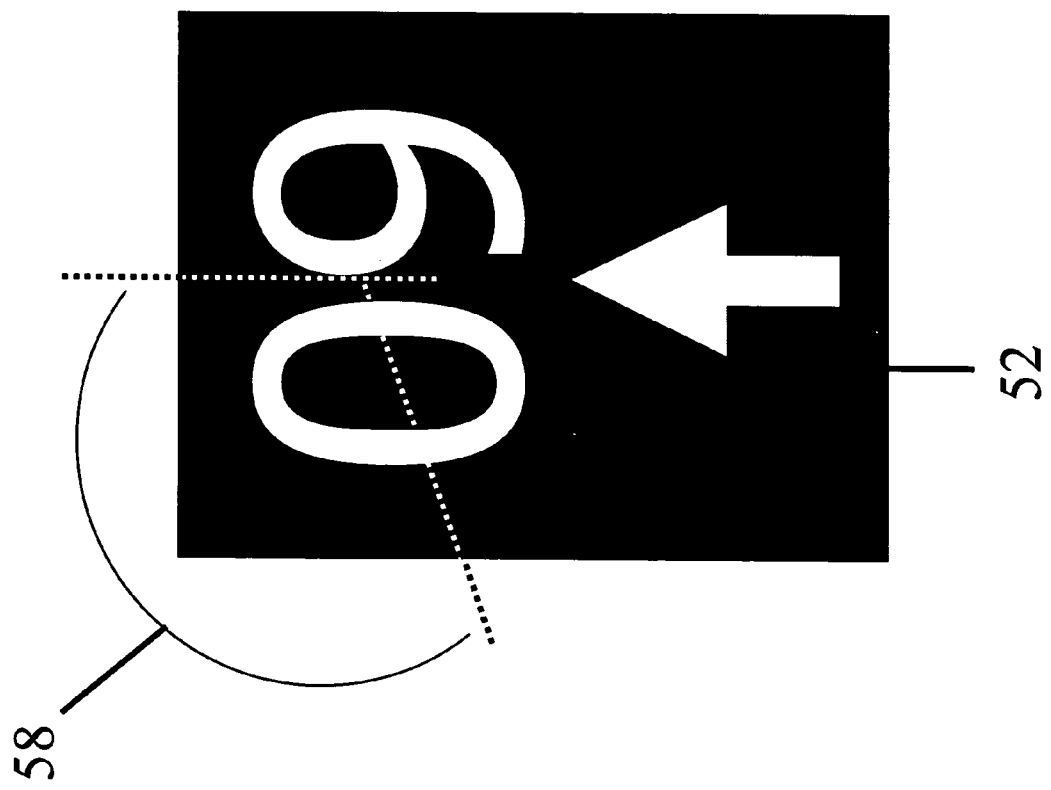
FIG. 7 is a schematic illustration of a PDI-enhanced sign with maximum contrast between the background (weak PDI return signal) and the lettering (strong PDI return signal), showing the area to be illustrated in FIGS. 8 and 9.
Figure 8:
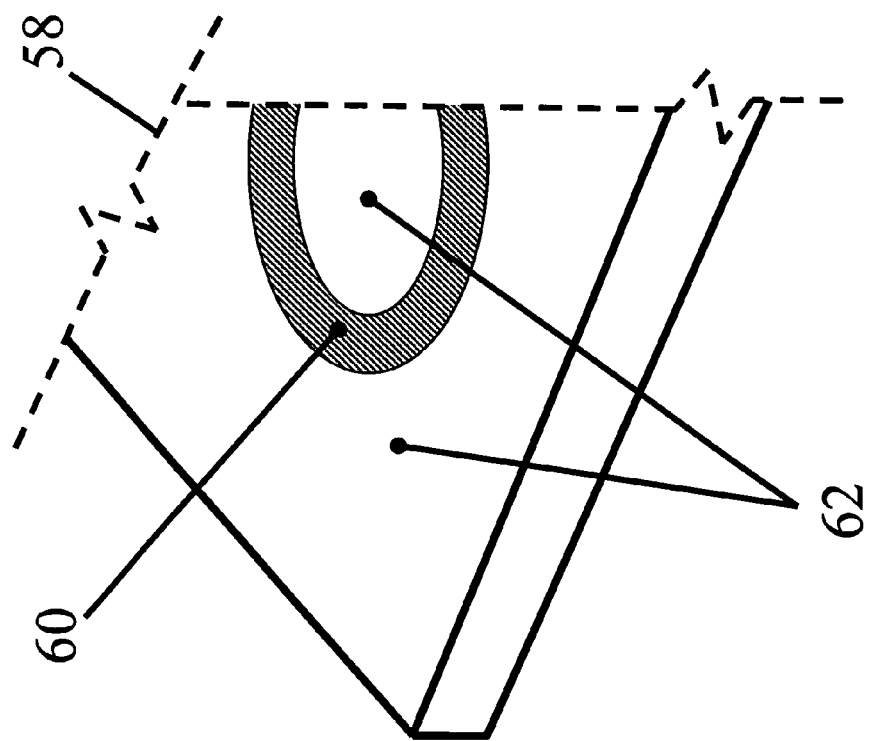
FIG. 8 illustrates a potential means of constructing a PDI-enhanced sign where areas of differential polarization reflectivity are created on a common structural substrate.
Figure 9:
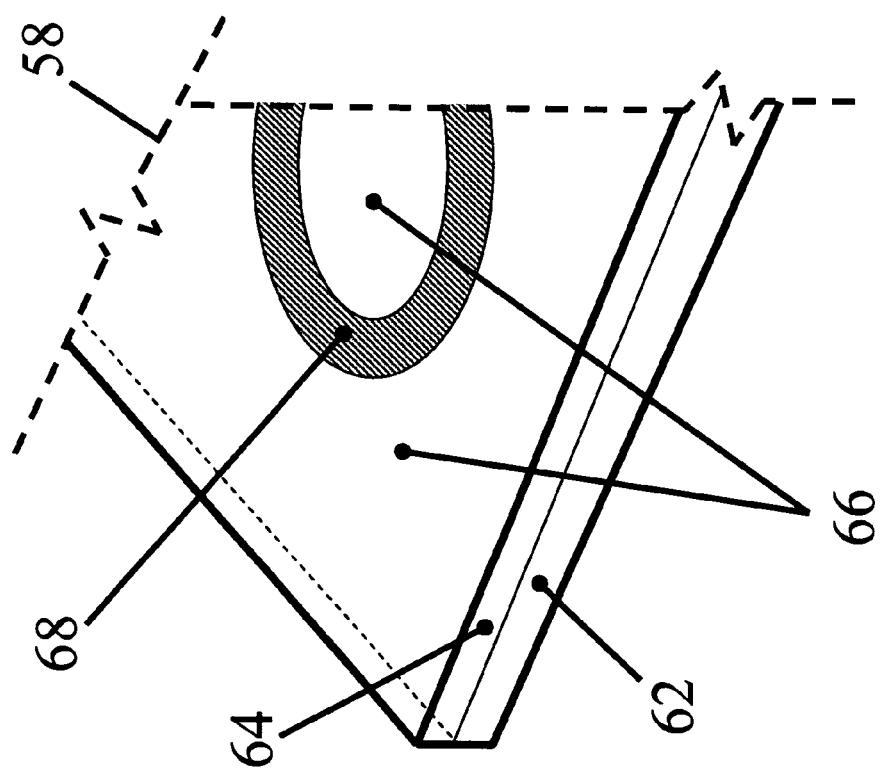
FIG. 9 illustrates a potential means of constructing a PDI-enhanced sign where areas of differential polarization reflectivity are created by a polarization selective mask over a reflective structural substrate.

As in FIG. 6, a PDI-enhanced sign (52) is illustrated which minimizes the return signal from the background, while increasing the signal strength and spatial resolution of symbols and lettering. The portion (58) of the sign delimited by the dashed lines will be used in FIGS. 8 and 9 to illustrate two potential methods for constructing a PDI-enhanced sign with these qualities.

FIG. 8.

This figure illustrates a portion of a PDI-enhanced sign (58), demonstrating one potential method of construction. In this example, both the region of polarization specific reflection (62) and the region of non-specific polarization reflection (60) are constructed on the same substrate. This could be accomplished by constructing the sign out of a material such as aluminium, and scoring its surface with shallow parallel linear grooves in the region where a polarization enhanced reflection is required (e.g. the lettering). Such grooves tend to both reflect polarized light having the same orientation of the grooves, as well as partially linearly polarizing ambient light reflected from the scored surface.

FIG. 9.

This figure illustrates a portion of a PDI-enhanced sign (58), demonstrating another potential method of construction. In this example, the sign is constructed by laminating a material (64) containing a region of polarization specific transmission (68) and a region of non-specific polarization transmission (66) over an underlying substrate that reflects all polarize stimuli equally. As a result, the non-specific polarization signal reflected from the background is rejected by the PDI process, and stands in stark contrast to the strong PDI signal returned from the polarization specific regions of the sign lettering.

Operation:

It can be seen from the descriptions above, that such a combined real-time polarization difference imaging video and illumination system can be used to, (1) enhance stimulus detection or image formation of an object in the presence of scattering medium or mechanisms, when the object is passively illuminated by a non-polarized stimuli (whereby the surface features of the target object imparts a partial polarization to the returned signal); (2) enhance stimulus detection or image formation of an object in the presence of scattering medium or mechanisms, when the object is illuminated by a polarized light source, thus maximizing the percentage of target-reflected polarized stimuli, (3) alter the mode of operation of the system to highlight and spatially map surface textures, deviations in surface geometry, or highlight corrosion on metal, and (4) enhanced throughput of polarized illumination system through utilizing reflection-induce polarization of an unpolarized light source prior to passing the light through a linear polarization filter (oriented to match the plane of polarization of the reflected beams).

Variations:

The underlying principles of the "real-time" PDI video imaging system, and the polarization illumination system, is not limited to visible wavelengths within the electromagnetic spectrum. Indeed, both infrared (IR) and microwave based systems would function, requiring only the appropriate stimulus sensors, emitters, and optical or wave-guide components for the range of operating wavelengths. As such, the examples given are meant for illustrative purposes of the general underlying principles, and do not define the scope of the claims. It is important to understand that the beams of light do not have to be within the visible spectrum.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one skilled in the art that modifications may be made to the illustrated embodiment without departing from the spirit and scope of the invention as hereinafter defined in the Claims.

What is claimed is:

1. An apparatus for real-time polarization difference imaging (PDI) video, comprising:

means for collimating stimulus light into parallel beams of light;

at least one polarizing beam splitter adapted to receive collimated beams of light and segregate orthogonally linearly polarized components of the beams of light;

at least two sensors for sensing the segregated orthogonally linearly polarized components of the beams of light, each of the segregated orthogonally linearly polarized components being directed at a different one of the at least two sensors;

means for computationally comparing one of the at least two sensors' output signal with another of the at least two sensors' output signal and creating a real-time polarization difference video signal.

2. The apparatus as defined in claim 1, wherein a polarized light source with a linear polarization orientation matching one of the orthogonal linearly polarized components Is used to illuminate a target.

3. The apparatus as defined in claim 2, wherein a light source is polarized for use as a polarized light source by a series of more than one reflection off reflecting surfaces.

4. The apparatus as defined in claim 2, wherein PDI-enhanced targets are provided with surface features adapted to maximize return signal strength and spatial contrast.

5. An apparatus for real-time polarization difference imaging (PDI) video, comprising:

a collimating lens;

at least one linearly polarizing beam splitter;

an imaging lens focusing stimulus beams of light onto the collimating lens, whereby the collimating lens causes the stimulus beams of light to become parallel before linearly striking the polarizing beam-splitter, the linearly polarized beam-splitter creating segregated orthogonally linearly polarized components of the stimulus beams of light;

at least two imaging sensors adapted to receive the segregated orthogonally linearly polarized components of the stimulus beams of light, each of the segregated orthogonally linearly polarized components being directed at a different one of the at least two sensors; and a processor adapted to receive input from the at least two imaging sensors and computationally compare one of the at least two imaging sensors' output signal with another of the at least two imaging sensors output signal to create a real-time polarization difference video signal.

6. A method of real-time polarization difference imaging (PDI), comprising the steps of:

collimating beams of light so that the stimulus beams of light become parallel;

passing the parallel beams of light through at least one linearly polarizing beam-splitter to segregate orthogonally linearly polarized components of the beams of light;

focusing the segregated orthogonally linearly polarized components of the beams of light upon at least two sensors, each of the segregated orthogonally linearly polarized components being directed at a different one of the at least two sensors;

computationally comparing one of the at least two sensors' output signal with another of the at least two sensors' output signal to create a real-time polarization difference video signal.

7. The method as defined in claim 6, including a step of illuminating a target with a linearly polarized light source having a polarization orientation matching that of one of the segregated orthogonally linearly polarized component.

8. The method as defined in claim 7, including a step of using PDI-enhanced targets having surface features adapted to maximize return signal strength and spatial contrast.

9. The method as defined in claim 6, the beams of light being selected from a range of wavelengths within a visible portion of the electro-magnetic spectrum.

10. The method as defined in claim 6, the beams of light being selected from a range of wavelengths outside of a visible portion of the electro-magnetic spectrum.

11. A method of real-time polarization difference imaging (PDI), comprising the steps of:

collimating beams of electromagnetic radiation so that the stimulus beams become parallel;

passing the parallel beams of electro-magnetic radiation through at least one linearly polarizing beam-splitter to segregate orthogonally linearly polarized components of the parallel beams;

focusing the segregated orthogonally linearly polarized components of the beams upon at least two sensors, each of the segregated orthogonally linearly polarized components being directed at a different one of the at least two sensors;

computationally comparing one of the at least two sensor's output signal with another of the at least two sensors' output signal to create a real-time polarization difference video signal.

* * * * *